United States Patent
Fukuda et al.

(10) Patent No.: US 9,710,731 B2
(45) Date of Patent: Jul. 18, 2017

(54) FOREIGN MATTER INSPECTION DEVICE AND FOREIGN MATTER INSPECTION METHOD

(75) Inventors: Hirohisa Fukuda, Hitachi (JP); Kunitaka Asano, Hitachi (JP); Tadahiro Katane, Hitachiota (JP); Hiromi Yamazaki, Hitachiota (JP)

(73) Assignee: Hitachi Information & Control Solutions, Ltd., Hitachi-shi (JP)

( * ) Notice: Subject to any disclaimer, the term of this patent is extended or adjusted under 35 U.S.C. 154(b) by 484 days.

(21) Appl. No.: 13/700,997

(22) PCT Filed: May 26, 2011

(86) PCT No.: PCT/JP2011/062097
§ 371 (c)(1),
(2), (4) Date: Nov. 29, 2012

(87) PCT Pub. No.: WO2011/152276
PCT Pub. Date: Dec. 8, 2011

(65) Prior Publication Data
US 2013/0070084 A1    Mar. 21, 2013

(30) Foreign Application Priority Data
May 31, 2010    (JP) ................ 2010-123649

(51) Int. Cl.
*G06K 9/78* (2006.01)
*G01N 21/90* (2006.01)

(52) U.S. Cl.
CPC ......... *G06K 9/78* (2013.01); *G01N 21/9018* (2013.01)

(58) Field of Classification Search
CPC .............. G06K 9/78; G01N 21/9018
(Continued)

(56) References Cited

U.S. PATENT DOCUMENTS

| 3,777,169 A | 12/1973 | Walter et al. | |
| 5,468,803 A * | 11/1995 | Takahashi et al. | 524/553 |

(Continued)

FOREIGN PATENT DOCUMENTS

| CN | 1693884 A | 11/2005 |
| CN | 101548178 A | 9/2009 |

(Continued)

OTHER PUBLICATIONS

International Search Report with English translation dated Aug. 30, 2011 (four (4) pages).

(Continued)

*Primary Examiner* — Thai Tran
*Assistant Examiner* — Nien-Ru Yang
(74) *Attorney, Agent, or Firm* — Crowell & Moring LLP (57) ABSTRACT

Disclosed are a foreign matter inspection device and a foreign matter inspection method, in which the accurate inspection of foreign matter is performed using captured images by continuous shooting in the state in which a movement locus due to the falling caused by the movement of the foreign matter along the inner wall of a container from the horizontal direction of the container as a result of rotation is formed so as to be long. A rotating device is provided with a rotation control means for executing the rotational motion in which container holding members for holding the container in a horizontal manner or at a constant inclination angle relative to the horizontal axis of the container, and the container are rotated at an angle of 60° or more, and then stopped, wherein a foreign matter detection means detects the foreign matter according to the movement locus of the foreign matter, which is formed using the captured images obtained by the continuous shooting for each rotational motion at constant time.

15 Claims, 6 Drawing Sheets

(58) Field of Classification Search
USPC .......................................................... 348/127
See application file for complete search history.

(56) References Cited

U.S. PATENT DOCUMENTS

| | | | |
|---|---|---|---|
| 5,694,221 A * | 12/1997 | Knapp | G01N 21/9027 250/223 B |
| 8,405,826 B2 | 3/2013 | Till et al. | |
| 2003/0063281 A1* | 4/2003 | Katane | G01N 21/9027 356/427 |
| 2003/0210397 A1* | 11/2003 | Yagita | 356/427 |
| 2003/0219490 A1* | 11/2003 | Hovey et al. | 424/489 |
| 2008/0001104 A1* | 1/2008 | Voigt et al. | 250/559.46 |
| 2008/0094618 A1* | 4/2008 | Sones et al. | 356/240.1 |

FOREIGN PATENT DOCUMENTS

| | | |
|---|---|---|
| EP | 1 298 428 A1 | 4/2003 |
| JP | 50-96491 A | 8/1975 |
| JP | 63-88431 A | 4/1988 |
| JP | 63-88433 A | 4/1988 |
| JP | 2-150752 A | 6/1990 |
| JP | 9-236553 A | 9/1997 |
| JP | 10-318940 A | 12/1998 |
| JP | 2003-107011 A | 4/2003 |
| JP | 2003-254912 A | 9/2003 |
| JP | 2004-257937 A | 9/2004 |
| JP | 2005-70013 A | 3/2005 |
| JP | 2007-78498 A | 3/2007 |
| JP | 2009-69099 A | 4/2009 |

OTHER PUBLICATIONS

Chinese Office Action dated Mar. 31, 2014, including partial English translation (eighteen (18) pages).
Japanese-language Office Action dated Apr. 2, 2013 with English translation (Five (5) pages0.
Japanese Office Action with partial English translation dated Jan. 7, 2014 (6 pages).

* cited by examiner

(A) START OF SPINNING
(B) END OF SPINNING
(C) STOP OF SPINNING

FOREIGN MATTER INSPECTION DEVICE AND FOREIGN MATTER INSPECTION METHOD

TECHNICAL FIELD

The present invention relates to a foreign matter inspection device and a foreign matter inspection method detecting foreign matter in liquid mixed into a container.

BACKGROUND ART

In order to detect foreign matter in a cylindrical container, for example minute foreign matter in an injection agent liquid in an ampoule, vial, syringe, and the like, a foreign matter inspection device is used. In detecting minute foreign matter, in the foreign matter inspection device, a whirling liquid stream is generated in liquid in a container around a vertical cylindrical container axis by spinning and the like, the minute foreign matter floating and moving in the liquid is photographed, picture difference data are analyzed, and the foreign matter is detected.

In Patent Literature 1, it is described that, in a foreign matter inspection device including an infrared irradiation device and an infrared imaging device picking up a fluoroscopic image of a container and an extracting means photographing movement of foreign matter at a predetermined temporal interval and extracting foreign matter images from the image data and, in rotating the container, adjusting the center axis of a container to a constant angle relative to the horizontal direction, the moving distance of the foreign matter is determined by acquiring information at every constant temporal unit, and a substance with heavy specific weight and settling quickly and a substance with specific weight close to that of the liquid and continuing a floating state are differentiated.

In Patent Literature 2, a foreign matter inspection device is described in which a container is rotated in a state a small diameter part of a container is supported in a generally horizontal manner, liquid in the small diameter part is temporarily moved to the container body side by a centrifugal force, rotation is thereafter stopped, and movement of foreign matter inside the container is detected by image processing.

RELATED ART DOCUMENT

Patent Document

[Patent Document 1] Japanese Unexamined Patent Application Publication No. 2004-257937
[Patent Document 2] Japanese Unexamined Patent Application Publication No. 2003-254912

SUMMARY OF INVENTION

Problems to be Solved by the Invention

In the Patent Literature 1, described is an example of detecting mixed-in foreign matter in a case red wine is contained in a bottle container.

On the other hand, there may be cases that an ampoule, vial, or syringe container is used as a container, the diameter of the container is small, the liquid quantity filled is small relative to the container capacity, the liquid is filled fully in the container, and the filled liquid is highly viscous such as an oily preparation for example. When the liquid is filled in the container in such the state and the container is made to spin vertically to generate a liquid stream in the liquid, there are cases that the liquid stream stops soon, the liquid itself hardly generates the liquid stream, the liquid stream is hardly generated in an end part and a corner part of the container, and movement of the foreign matter is dull and detection of the moving foreign matter by image processing is difficult.

Figure 7A:
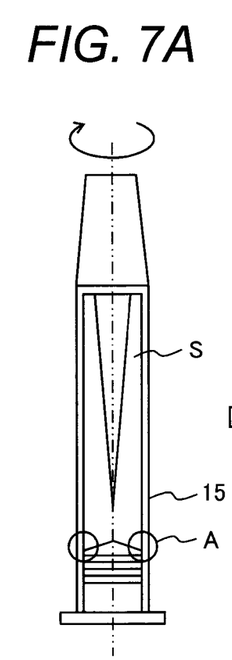
FIG. 7 is an explanatory drawing showing a case a standing rotating container is photographed in an example of a prior art.
Figure 7B:
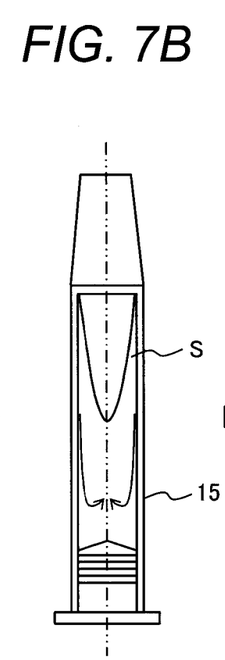
Figure 7C:
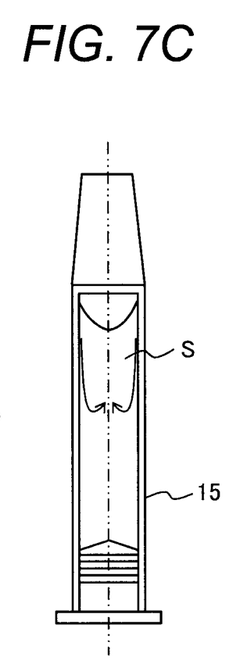

FIG. 7 explains a problem accompanying movement of foreign matter in a case of photographing while a container is erected in an example of a prior art. In step (A), when a container 15 is rotated (is spun), liquid S rotates accompanying rotation of the container, and the liquid surface of a circular cone shape is generated. When rotation is stopped in step (B), in the liquid S, a liquid stream returning downward from the inner wall of the container is generated accompanying reduction of inertial rotation. In step (C), the velocity of the fluid further drops, and the liquid surface is restored. In a state the liquid stream is hardly generated, for example when the diameter of the container is small, the quantity of liquid filled is small, and liquid filled is highly viscous such as an oily preparation for example, the event that only the liquid moves by inertia after spinning stops does not occur, and the liquid stream stops soon. Also, even when the liquid stream is generated, movement is dull, and the liquid stream itself is hardly generated at the bottom part of the container and the corner part A thereof.

Accordingly, when foreign matter with larger specific gravity than that of the liquid (for example a glass piece, a metal piece and the like) is present in particular, the foreign matter comes to settle at the bottom part of the container, and when the container is made spin in order to move the foreign matter as done in the prior art, the foreign matter moves to the corner of the bottom part, therefore the condition for moving the foreign matter deteriorates, and required movement of the foreign matter cannot be expected.

As a solving method thereof, it can be devised that, as shown in the Patent Literature described above, a container is arranged in a horizontal manner or at an inclination angle and is rotated by 2-3 turns, and thereby foreign matter having some specific gravity is made to slip downward along the inner wall of the container by gravity to the direction opposite to the rotational direction and is thereby photographed.

With respect to this solving method, in such a case of a container with a large diameter and liquid with low viscosity as red wine, moving speed and moving distance of the foreign matter in the liquid can be expected, and it is effective in differentiating foreign matter settling quickly and foreign matter floating. However, when the diameter of the container is small, the liquid quantity filled is small, the liquid is filled fully in the container, and the liquid filled is highly viscous such as an oily preparation for example, according to the angle of rotation of the container, it is not possible to surely move the foreign matter along the inner wall of the container and to secure the moving distance, which cannot become an effective solving method that can surely detect minute foreign matter by using a means measuring and determining the moving distance of the foreign matter.

Also, it is not possible to effectively detect foreign matter whose falling speed is slow because the liquid stream is hardly generated and the moving is dull due to the viscosity of liquid or the specific gravity of the foreign matter.

In view of such circumstances, the object of the present invention is to provide a foreign matter inspection device capable of inspection even when the diameter of the container to be used is small, the liquid quantity filled is small, and the liquid filled is highly viscous such as an oily preparation for example, and movement of the foreign matter is dull because the liquid stream stops soon, the liquid itself hardly generates the liquid stream, and the liquid stream is hardly generated to the end part, or with respect to the foreign matter with high specific gravity also.

Means for Solving the Problems

The present invention is a foreign matter inspection device, including container holding members that hold cylindrical containers filled with liquid, rotating devices that rotate the containers, irradiating photographing devices that irradiate an irradiation beam to the containers and photograph foreign matter mixed in the liquid in the containers, and a foreign matter detecting unit that detects the foreign matter from photographed images, in which the rotating device includes a rotation control unit that makes the container holding member that holds a center shaft of the container in a horizontal manner or at a constant inclination angle and the container execute a rotational motion of rotating at a rotational angle of a range of ±60° or more and ±180° or less and then stopping, the irradiating photographing device executes photographing by continuous shooting while stopping after rotating accompanying rotation of the containers, and the foreign matter detecting unit detects the foreign matter using photographed images acquired by continuous shooting for each rotational motion with a predetermined constant time according to a foreign matter movement locus formed from the photographed images.

Also, in the foreign matter inspection device, the foreign matter detecting unit executes the rotational motion plural times, and executes photographing by continuous shooting at every stopping after each rotation.

Also, in the foreign matter inspection device, rotational angle of the containers is set to a range of ±60° or more and ±120° or less.

Also, in the foreign matter inspection device, rotational angle of the containers is set to a range of ±60° or more and ±90° or less.

Also, in the foreign matter inspection device, rotational angle of the containers is set to ±60°.

Also, in the foreign matter inspection device, the container is any one of an ampoule, vial, or syringe, and the inside diameter of the container is 2 to 20 mm.

Also, in the foreign matter inspection device, the container is any one of an ampoule, vial, or syringe, and quantity of liquid in the container is 10% or less of a filling possible capacity.

Also, in the foreign matter inspection device, the container is any one of an ampoule, vial, or syringe, and includes highly viscous liquid with 20 mPa·s-2 Pa·s viscosity.

Also, a foreign matter inspection method for rotating cylindrical containers filled with liquid, irradiating an irradiation beam to the containers and photographing foreign matter mixed in liquid in the containers, and detecting the foreign matter from photographed images includes the steps of holding a center shaft of the container in a horizontal manner or at a constant inclination angle and making the container execute a rotational motion of rotating at a rotational angle of a range of ±60° or more and ±180° or less and then stopping, photographing by continuous shooting while stopping after rotation of the containers, and detecting the foreign matter using photographed images acquired by the continuous shooting for each rotational motion with a predetermined constant time according to a foreign matter movement locus formed from the photographed images.

Also, in the foreign matter inspection method, the rotational motion of the containers is executed plural times, and photographing by continuous shooting at every stopping after each rotation is executed.

Also, in the foreign matter inspection method, rotational angle of the containers is set to a range of ±60° or more and ±120° or less.

Also, in the foreign matter inspection method, rotational angle of the containers is set to a range of ±60° or more and ±90° or less.

Also, in the foreign matter inspection method, rotational angle of the containers is set to a range of ±60°.

Also, in the foreign matter inspection method, the container is any one of an ampoule, vial, or syringe, and the inside diameter of the container is 2 to 20 mm.

Also, in the foreign matter inspection method, the container is any one of an ampoule, vial, or syringe, and quantity of liquid in the container is 10% or less of a filling possible capacity.

Also, in the foreign matter inspection method, the container is any one of an ampoule, vial, or syringe, and includes highly viscous liquid with 20 mPa·s-2 Pa·s viscosity.

Effects of Invention

According to the present invention, in a foreign matter inspection device including container holding members that hold cylindrical containers, rotating devices that rotate the containers, an irradiating photographing device that photograph foreign matter, and a foreign matter detecting unit that detects the foreign matter from a photographed image, the rotating device includes a rotation control unit that makes the container holding member that holds a center shaft of the container in a horizontal manner or at a constant inclination angle and the container execute a rotational motion of rotating at an angle of ±60° or a range of ±60° or more and ±180° or less and then stopping, the irradiating photographing device photographs by continuous shooting while stopping after rotating accompanying rotation of the containers is executed, and the foreign matter detecting unit detects the foreign matter using photographed images acquired by continuous shooting for each rotational motion according to a foreign matter movement locus formed from the photographed images, and thereby easy detection is allowed even when the diameter of the containers to be used is small, the liquid quantity filled is small, the liquid filled is highly viscous such as an oily preparation for example, the liquid stream is hardly generated and movement of the foreign matter is dull, and with respect to the foreign matter with high specific gravity and the like also.

DESCRIPTION OF EMBODIMENTS

The foreign matter inspection device of the present invention is characterized that foreign mater is detected not by measuring the moving distance of the foreign matter as done in an example of a prior art but by forming a movement locus of the foreign matter using photographed images. Below, an example of the present invention will be described based on the drawings.

EXAMPLE

Figure 1:
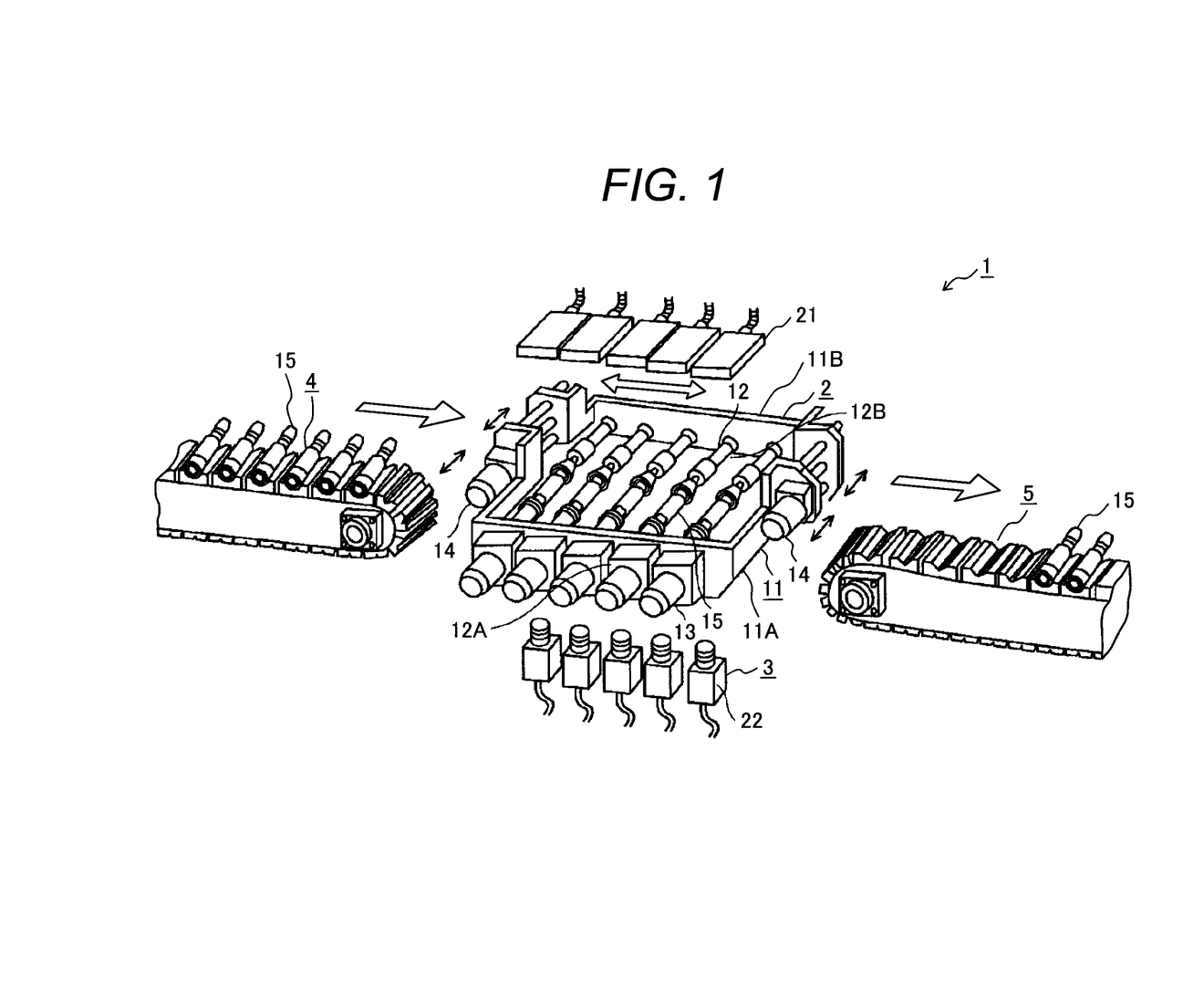
FIG. 1 is a perspective view showing a total constitution of a foreign matter inspection device in an example of the present invention.

FIG. 1 is a drawing showing a total constitution of a foreign matter inspection device which is an example of the present invention. In FIG. 1, a foreign matter inspection device 1 is composed of an inspection device body 2 and irradiating photographing devices 3, and container conveying devices 4, 5 are arranged respectively on both right and left sides of the inspection device body 2.

The inspection device body 2 is composed of plural container holding members 12 arranged inside a frame 11, rotating devices 13 rotating the container holding members 12 respectively, and a pair of frame connecting devices 14 attached to the frame 11.

The frame 11 includes a right frame 11A and a left frame 11B which are connected to each other by the frame connecting devices 14. The frame connecting device 14 includes a piston-cylinder mechanism and an operation mechanism therefor, and the connection distance can be elongated and contracted by the piston-cylinder.

The container holding member 12 includes a container mounting part 12A arranged on the right side and a container supporting part 12B arranged on the left side with respect to the container conveying direction, and holds a container 15 such as an ampoule, vial, syringe and the like therebetween.

The container 15 is held on the container holding member 12 in a horizontal manner or at a constant inclination angle with respect to a horizontal axis of the container, and is rotated by the rotating device 13.

The rotating device 13 includes a rotation control unit (not shown) that controls rotation of the container holding members 12. Rotation control is executed by computer control in which a program is incorporated.

The container conveying device 4 is a device that carries the containers 15 before inspection into the inspection device body 2, and is composed of a conveyor conveying the containers 15 placed horizontally and a drive system therefor. The containers 15 are arrayed with regularity in respective grooves arranged on the conveyor and are conveyed.

The container conveying device 5 is a device that takes out the containers 15 after inspection from the inspection device body 2, and the constitution thereof is similar to that of the container conveying device 4.

When the containers are taken out by the container conveying device 5 and the containers are carried in by the container conveying device 4, right and left sections of the frame 11 are largely opened to the right and left by the frame connecting devices 14, and the container mounting parts 12A and the container supporting parts 12B of the container holding members 12 are largely moved to the right and left accompanying it. Accompanying the movement, supporting of the containers 15 by the container supporting parts 12B is released, and the containers 15 are held only by the container mounting parts 12A. Under such a state, the container holding members 12 are moved onto the container conveying device 5 by a container built-in device not shown, and the containers 15 are mounted on the conveyor of the container conveying device 5.

Next, the containers 15 on the conveyor of the container conveying device 4 are mounted on the respective container mounting parts 12A. In the mounting, distal ends of the container mounting parts 12A are fitted to the tail portions of the containers 15, then the interval is narrowed by the frame connecting devices 14, and the head portions of the containers 15 are supported by the container supporting parts 12B, and the containers 15 are thereby fixed. Thus, the respective container supporting members 12 or the respective containers 15 are rotated.

The irradiating photographing device 3 is composed of plural irradiation beam irradiating devices 21 arranged above the inspection device body 2 and plural photographing devices 22 arranged below, and the photographing devices 22 are connected to a foreign matter detecting unit (not shown) through signal lines. The photographing devices 22 and the foreign matter detecting unit may be integrated with each other.

The foreign matter detecting unit detects foreign matter from photographed image data. To determine foreign matter from photographed images and to detect the foreign matter are commonly known in this field. With respect to the irradiation beam, not only the infrared but also visible light can be used, and transmitted light or reflected light can be used.

Figure 2:
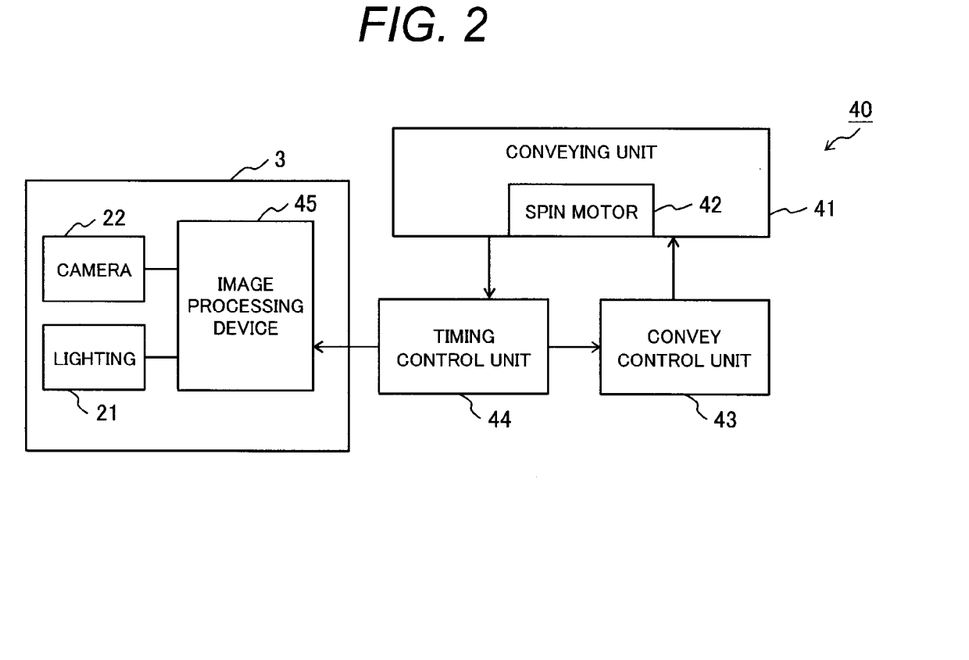
FIG. 2 is a block diagram showing a timing controller of a foreign matter inspection device in an example of the present invention.

FIG. 2 shows a constitution of a control device of the foreign matter inspection device 1 which is an example of the present invention by a block diagram.

In FIG. 2, a timing controller 40 includes a spin motor 42, and is composed of convey control units 43 inside the container conveying devices 4, 5, a timing control unit 44, an image processing device 45 composing the foreign matter detecting unit, the photographing devices 22 including cameras and the like, and the irradiation beam irradiating devices 21 including lightings and the like. The irradiating photographing device 3 is formed of the irradiation beam irradiating device 21, the photographing device 22, and the image processing device 45.

A control signal from the timing control unit 44 is transmitted to the convey control units 43 as rotation control units and the control signal is formed. The control signal is transferred to a conveying unit 41, and the spin motor 42 is rotation-controlled and is rotated and stopped. This signal is transmitted to the timing control unit 44, the image processing device 45 as the foreign matter detecting unit is activated, the irradiation beam irradiating device 21 and the photographing device 22 work, continuous photographed images are acquired by the image processing device 45, and presence of the foreign matter is detected. The spin motor 42 controls the rotational angle and rotational speed of the container holding member 12.

Figure 3:
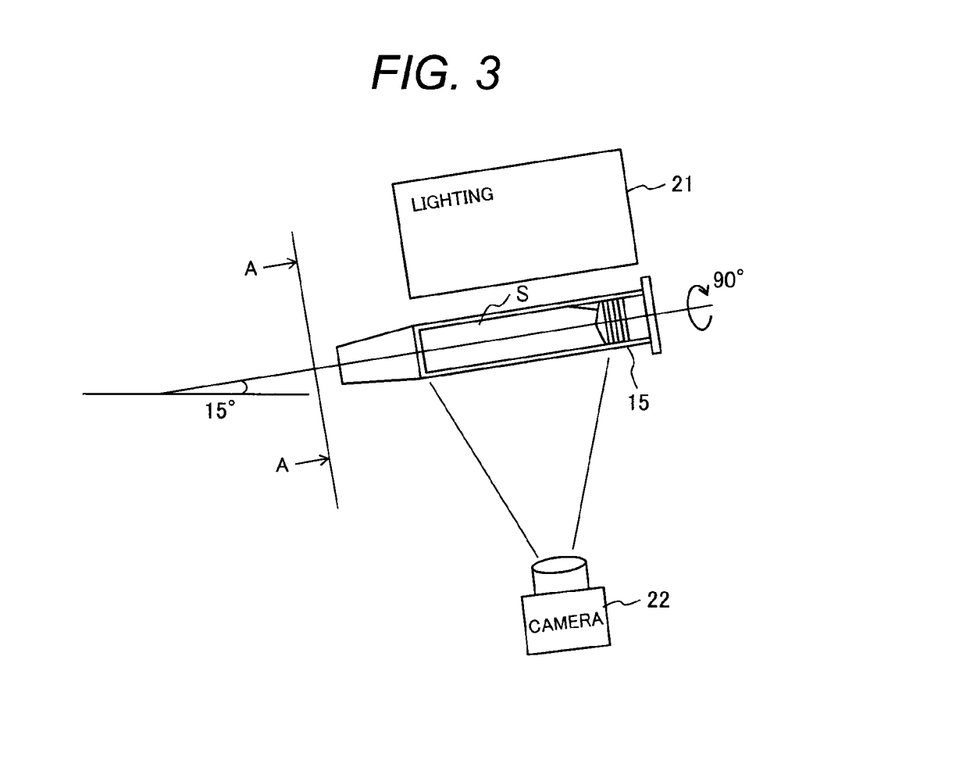
FIG. 3 is a schematic drawing showing a configuration of photographing a container by a photographing device in an example of the present invention.
Figure 4:
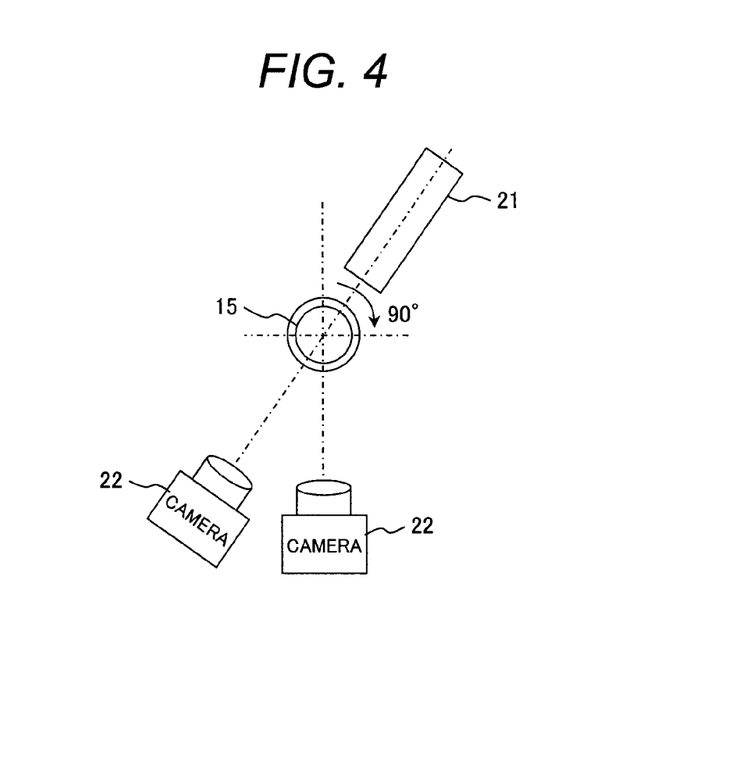
FIG. 4 is a drawing as viewed along arrows A-A in FIG. 3.

FIG. 3 shows a state of photographing the container 15 by the photographing device 22, and FIG. 4 is a drawing as viewed along arrows A-A in FIG. 3.

In these drawings, the container 15 is held in a horizontal manner or at an inclination relative to the horizontal plane (15° in the example of FIG. 3, however the inclination angle changes according to the liquid property and the shape of the container), and the container is rotated by a constant angle around the axis of the cylinder. The rotational angle is 90° in the example of FIG. 6, however it changes according to the liquid property and the shape of the container.

Then, the foreign matter settled on the inner wall of the container moves accompanying rotation of the container 15. In the movement, the foreign matter having specific gravity larger than that of the liquid slides down further downward along the inner wall of the container by gravity to the direction opposite to the rotational direction. At this time, rotation is stopped to bring the container to a standstill, and plural images are photographed by continuous shooting by the photographing device 22 with a constant shooting time. The movement locus of the foreign matter is formed using the photographed images, and detection of the foreign matter is thereby allowed.

The condition of the container, liquid, and foreign matter actually used is as described below.
(1) Inside diameter of container: 8 (mm)
(2) Liquid length inside container: 50 (mm)
(3) Material of container: COP resin
(4) Viscosity of liquid: 40 m (Pa·s)
(5) Specific gravity of liquid: 1.5
(6) Specific gravity of foreign matter: 4.5 (stainless steel)
(7) Rotational speed of container: 200 (rpm)

The condition described above is one example, and the effect is exerted in the range described below for example in the present invention.
(1) Inside diameter of container: 1-20 (mm)
(2) Liquid length inside container: 5-50 (mm)
(3) Material of container: PP, PE, PET, COC, COP, glass
(4) Viscosity of liquid: 20 m (Pa·s)-2 (Pa·s)
(5) Specific gravity of liquid: 1-3
(6) Specific gravity of foreign matter: 2-6 (glass, metal)
(7) Rotational speed of container: 100-2,000 (rpm)

In FIG. 4, with respect to the arranging angle of the camera that is the photographing device 22, it may be right under the container 15, and the camera may be arranged at an angle relative to the rotational direction of the container.

Figure 5:
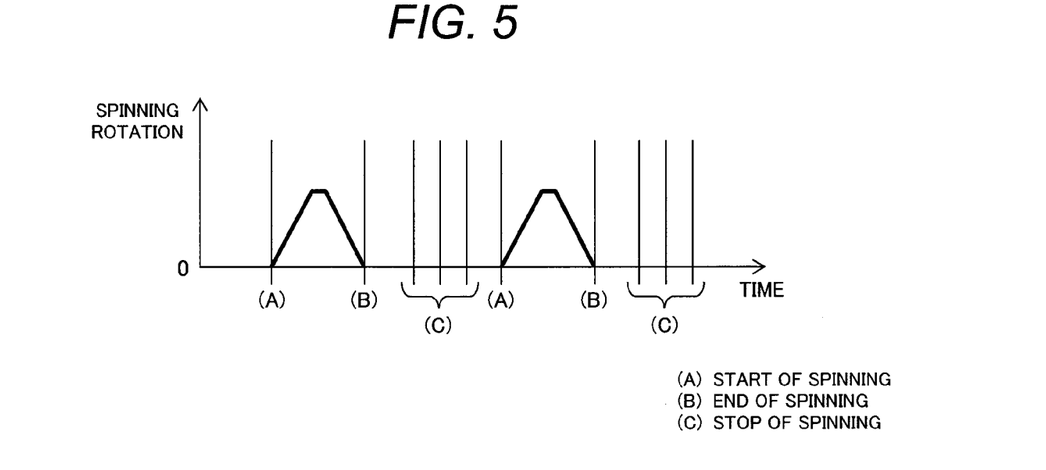
FIG. 5 is an explanatory drawing showing a method for photographing foreign matter in an example of the present invention.

In the present example, rotation control shown in FIG. 5 is employed. The rotation control unit makes the container 15 execute the rotational motion of spinning (revolving) by an angle of 60° or more, for example 90°, and then stopping twice or more. The foreign matter detecting unit detects foreign matter using the foreign matter movement locus formed from the images acquired by continuous shooting at every rotational motion using the images. Detection of the moving distance is possible when the image is shifted by three pixels or more in the photographing device. Thus, the foreign matter detecting unit detects the foreign matter using photographed images acquired by continuous shooting at every rotational motion with a predetermined constant shooting time by a foreign matter movement locus formed from the photographed images.

In FIG. 5, (A) shows the start of spinning, (B) shows the end of spinning, (C) shows a spinning stopping state, and a state the container 15 is rotated twice by an angle of 90° is shown. When the container 15 is rotated twice by an angle of 90°, wherever the initial position of the foreign matter may be, the foreign matter can move to the upper part of the inner wall of the container with a constant shooting time by at least one of the rotation, therefore the foreign matter movement locus with which the foreign matter falls down along the inner wall of the container by gravity can be acquired. The time between (A) and (B) is set longer as the viscosity of the liquid is higher.

Figure 6A:
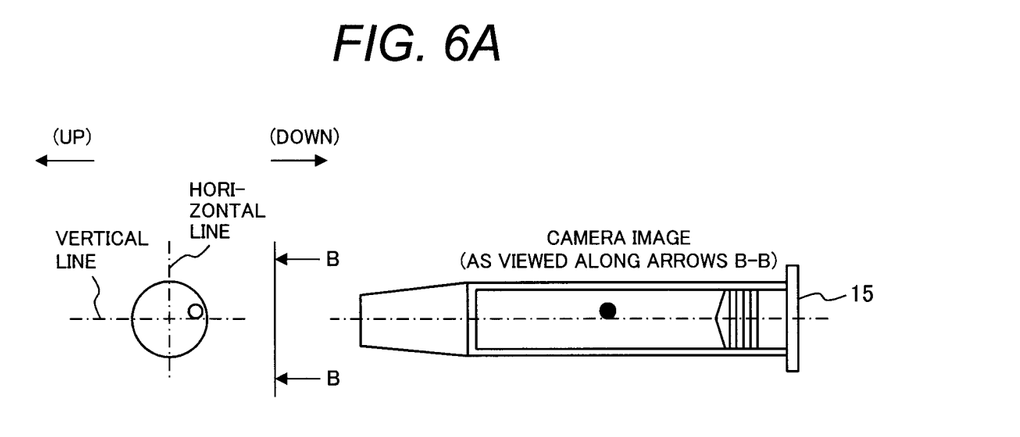
FIG. 6A is a schematic drawing showing a camera image of a state (A) in FIG. 5.
Figure 6B:
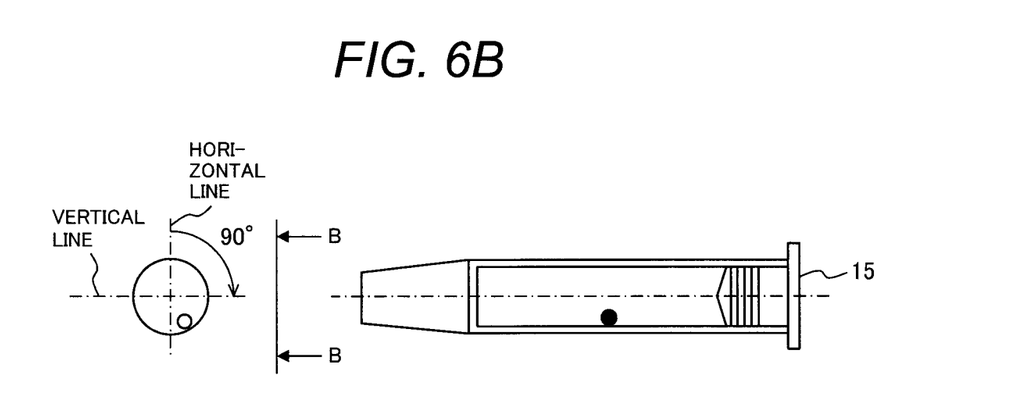
FIG. 6B is a schematic drawing showing a camera image of a state (B) in FIG. 5.
Figure 6C:
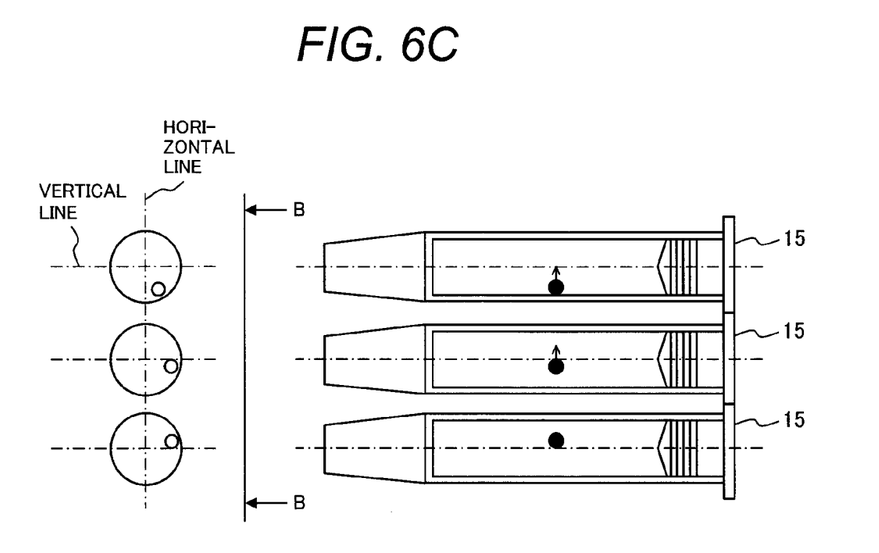
FIG. 6C is a schematic drawing showing a camera image of a state (C) in FIG. 5.
Figure 6D:
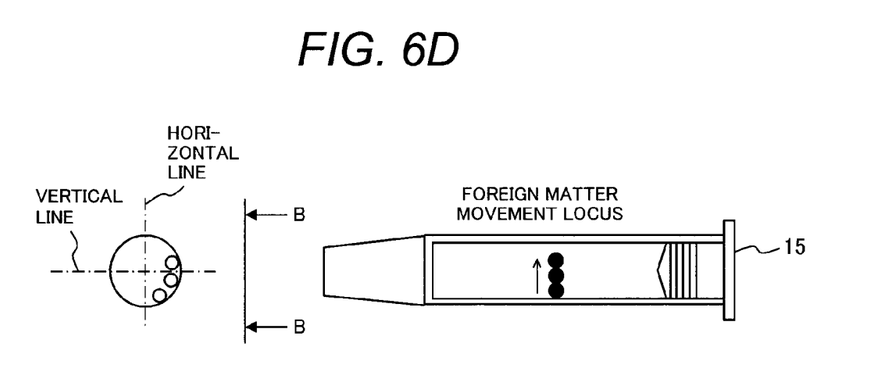
FIG. 6D is a schematic drawing showing a foreign matter movement locus.

FIGS. 6A-6D are schematic drawings showing the container 15 as viewed in the arrows B-B direction upward from the bottom face. FIG. 6A is a camera image at the time of (A) the start of spinning in FIG. 5, FIG. 6B is a camera image at the time of (B) the end of spinning, FIG. 6C is a camera image at the time of (C) stopping of spinning. FIG. 6D shows the foreign matter movement locus in which the longest moving distance was obtained out of the images photographed while the container 15 was rotated plural times.

Accordingly, wherever case the container 15 is in, by rotating the container 15 by a predetermined angle, photographing becomes possible, and the photographed image of the case the longest movement locus has been obtained can be selected. Here, what is important is that the foreign matter is moved to the upper part of the inner wall of the container, and, when the rotation angle is large, the foreign material can be moved to a desired position at one time, and the foreign matter movement locus can be photographed. On the other hand, when the rotation angle is small, there is also an effect that the foreign matter becomes easy in moving while rotation and photographing are repeated plural times.

As described above, even when the container is an ampoule, vial or syringe container and the liquid inside the container is a highly viscous liquid such as an oily preparation, the foreign matter can be detected effectively.

EXPLANATION OF REFERENCE

1 . . . foreign matter inspection device, 2 . . . inspection device body, 3 . . . irradiating photographing device, 4, 5 . . . container conveying device, 11 . . . frame, 12 . . . container holding member, 13 . . . rotating device, 15 . . . container, 21 . . . irradiation beam irradiating device, 22 . . . photographing device, 45 . . . image processing device

The invention claimed is:
1. A foreign matter inspection device, comprising:
container holders that hold cylindrical containers filled with liquid;
rotators that rotate the containers;
beam irradiators that irradiate a beam to the containers;
cameras that photograph foreign matter mixed in liquid in the containers;
a rotation controller; and
a foreign matter detector that detects the foreign matter from photographed images, wherein, when the foreign matter inspection device inspects the liquid in a selected one of the containers,
one of the holders holds the selected container so that a rotational axis, about which the selected container rotates, extends horizontally or at a constant acute angle of up to 15° depending on liquid properties and a shape of the selected container relative to a horizontal plane,
the rotation controller rotates the selected container through a selected rotational angle or speed to move the foreign matter upward in the vertical direction along with an inner wall of the container, after each rotation through said selected rotational angle or speed, thereby moving the foreign matter upward of said inner wall of the selected container, and stops rotation of the selected container, the cameras continuously photograph contents of the container for a predetermined time period each time the selected container is stopped from rotating, and the foreign matter detector acquires any existing foreign matter movement locus from images produced as the contents of the container are continuously photographed for the predetermined time period, and detects presence of the foreign matter in the liquid when the foreign matter movement locus exists.

2. The foreign matter inspection device according to claim 1, wherein the cameras continuously photographs said contents after each rotation.

3. The foreign matter inspection device according to claim 1, wherein the selected rotational angle is set to a range of ±60° or more and ±120° or less.

4. The foreign matter inspection device according to claim 1, wherein the selected rotational angle is set to a range of ±60° or more and ±90° or less.

5. The foreign matter inspection device according to claim 1, wherein the selected rotational angle is set to ±60°.

6. The foreign matter inspection device according to claim 1, wherein the selected container is any one of an ampoule, a vial, or a syringe, and the inside diameter of the selected container is 2 to 20 mm.

7. The foreign matter inspection device according to claim 1, wherein the selected container is any one of an ampoule, a vial, or a syringe, and a quantity of the liquid in the selected container is 10% or less of a filling possible capacity.

8. The foreign matter inspection device according to claim 1, wherein the selected container is any one of an ampoule, a vial, or a syringe, and the liquid is a highly viscous liquid with 20 mPa·-2 Pa·s viscosity.

9. A foreign matter inspection method for rotating cylindrical containers filled with liquid, irradiating an irradiation beam to the containers, photographing foreign matter mixed in liquid in the containers, and detecting the foreign matter from photographed images, comprising the steps of:

holding a selected one of the containers so that a rotational axis about which the selected container rotates extends horizontally or at a constant acute angle of up to 15° depending on liquid properties and a shape of the selected container relative to a horizontal plane;

rotating the selected container through a selected rotational angle or speed to move the foreign matter upward in the vertical direction along with an inner wall of the container, after each rotation through said selected rotational angle or speed, thereby moving the foreign matter upward of said inner wall of the selected container, and stopping rotation of the container;

continuously photographing contents of the selected container for a predetermined time period each time the selected container is stopped from rotating and the foreign matter moves in a downward vertical direction along with the inner wall of the selected container;

acquiring any existing foreign matter movement locus from the images produced as the contents of the container are continuously photographed for the predetermined time period; and detecting presence of the foreign matter in the liquid when the foreign matter movement locus exists.

10. The foreign matter inspection method according to claim 9, wherein the selected rotational angle is set to a range of ±60° or more and ±120° or less.

11. The foreign matter inspection method according to claim 9, wherein the selected rotational angle is set to a range of ±60° or more and ±90° or less.

12. The foreign matter inspection method according to claim 9, wherein the selected rotational angle is set to a range of ±60°.

13. The foreign matter inspection method according to claim 9, wherein the selected container is any one of an ampoule, a vial, or a syringe, and the inside diameter of the selected container is 2 to 20 mm.

14. The foreign matter inspection method according to claim 9, wherein the selected container is any one of an ampoule, a vial, or a syringe, and a quantity of the liquid in the selected container is 10% or less of a filling possible capacity.

15. The foreign matter inspection method according to claim 9, wherein the selected container is any one of an ampoule, vial, or syringe, and the liquid is a highly viscous liquid with 20 mPa·s-2 Pa·s viscosity.

* * * * *